(12) United States Patent
Blickhan et al.

(10) Patent No.: US 6,742,760 B2
(45) Date of Patent: Jun. 1, 2004

(54) FLOW CONTROL DEVICE

(75) Inventors: Bryan Blickhan, Zion, IL (US); Ying-Cheng Lo, Green Oaks, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/964,959

(22) Filed: Sep. 27, 2001

(65) Prior Publication Data

US 2003/0057390 A1 Mar. 27, 2003

(51) Int. Cl.[7] ............................................... F16K 31/00
(52) U.S. Cl. ......................................................... 251/11
(58) Field of Search ............................. 257/10, 9, 7, 4; 604/250; 137/271

(56) References Cited

U.S. PATENT DOCUMENTS

| | | | | |
|---|---|---|---|---|
| 485,698 A | * | 11/1892 | Ketchum | 251/9 |
| 2,954,028 A | * | 9/1960 | Smith | 604/250 |
| 3,316,910 A | * | 5/1967 | Davis | 251/9 |
| 3,316,935 A | * | 5/1967 | Kaiser et al. | 251/4 |
| 3,942,228 A | | 3/1976 | Buckman et al. | |
| 4,588,160 A | * | 5/1986 | Flynn et al. | 251/10 |
| 4,643,389 A | * | 2/1987 | Elson et al. | 251/10 |
| 4,801,050 A | * | 1/1989 | Bell | 251/9 |
| 5,402,823 A | * | 4/1995 | Cole | 251/9 |
| 5,423,769 A | * | 6/1995 | Jonkman et al. | 604/250 |
| 5,429,615 A | * | 7/1995 | Starchevich | 251/10 |
| 5,460,204 A | * | 10/1995 | Rossi | 137/271 |
| 5,910,135 A | * | 6/1999 | Hadzic et al. | 604/251 |
| 6,089,527 A | | 7/2000 | Utterberg | |
| 6,113,062 A | | 9/2000 | Schnell et al. | |

FOREIGN PATENT DOCUMENTS

| | | |
|---|---|---|
| WO | WO 00/24313 A1 | 5/2000 |
| WO | WO 01/08546 A2 | 2/2001 |

* cited by examiner

Primary Examiner—John Bastianelli
(74) Attorney, Agent, or Firm—Andrew Kolomayets; Michael Mayo

(57) ABSTRACT

Devices for controlling the flow of fluid through plastic tubes, such as tubes which are part of a disposable blood donation tubing set are disclosed. The device has a clamp adapted for attachment with one or more other clamps to allow for easy flow control through two or more tubing segments.

24 Claims, 5 Drawing Sheets

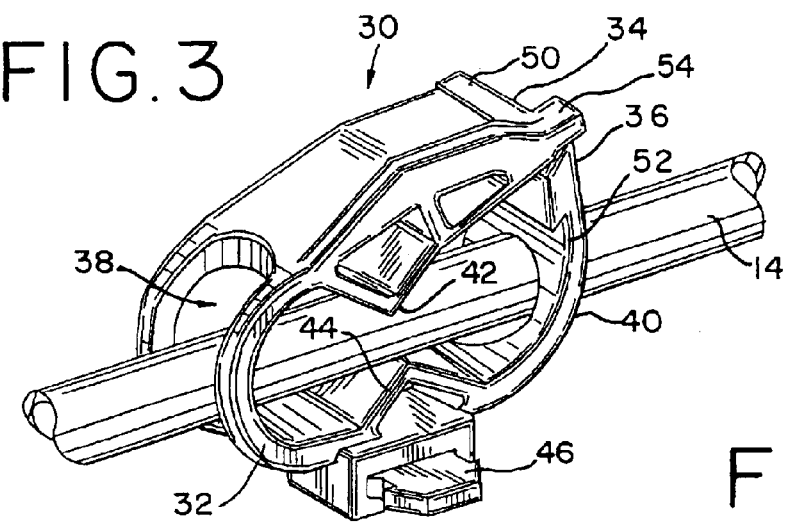
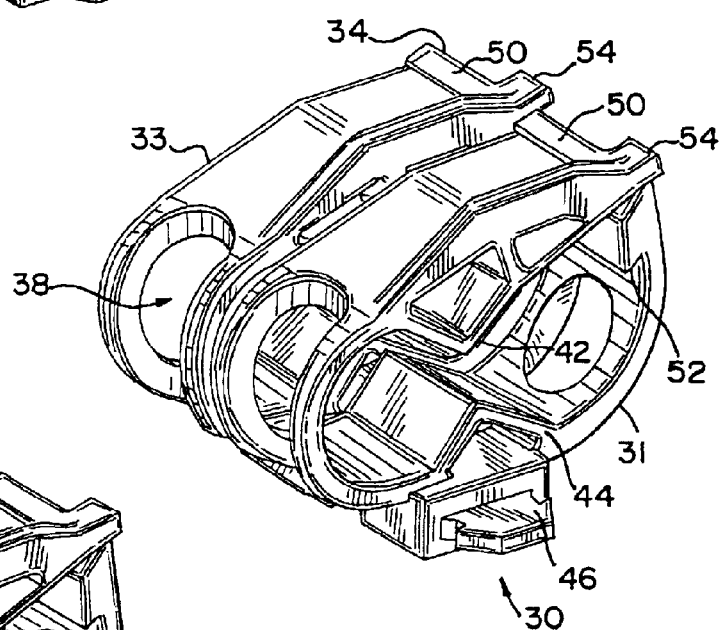
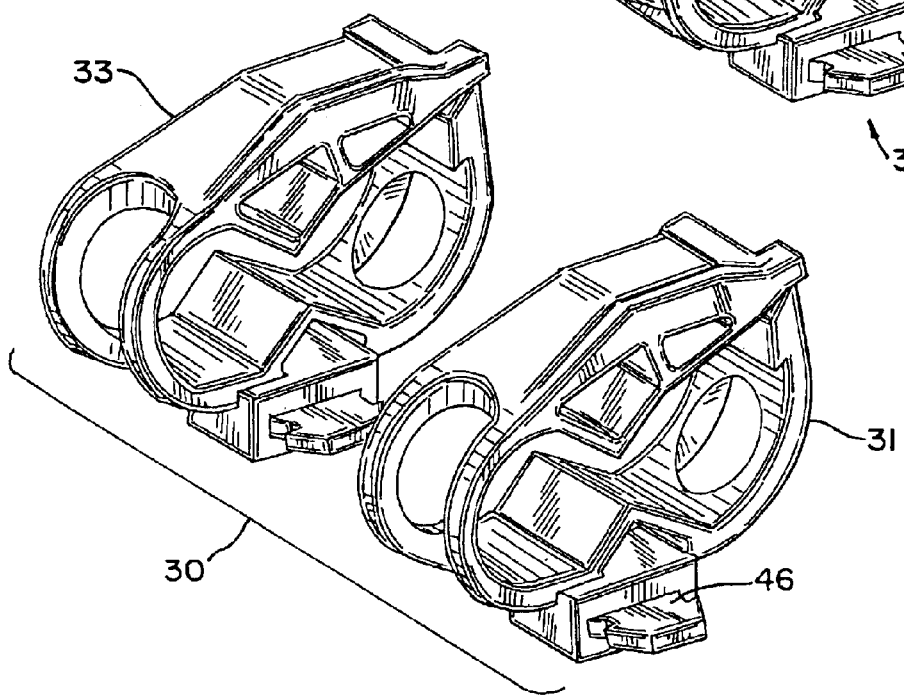

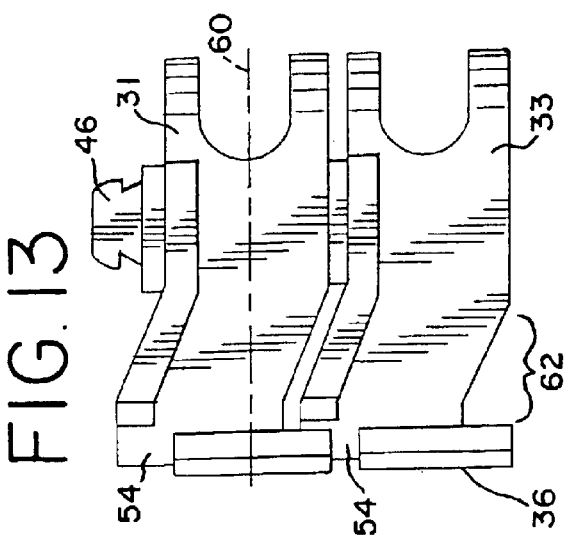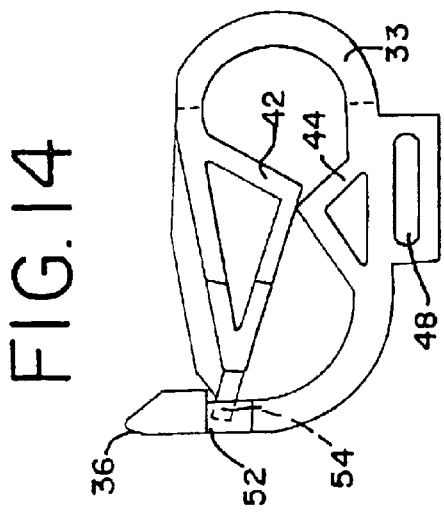

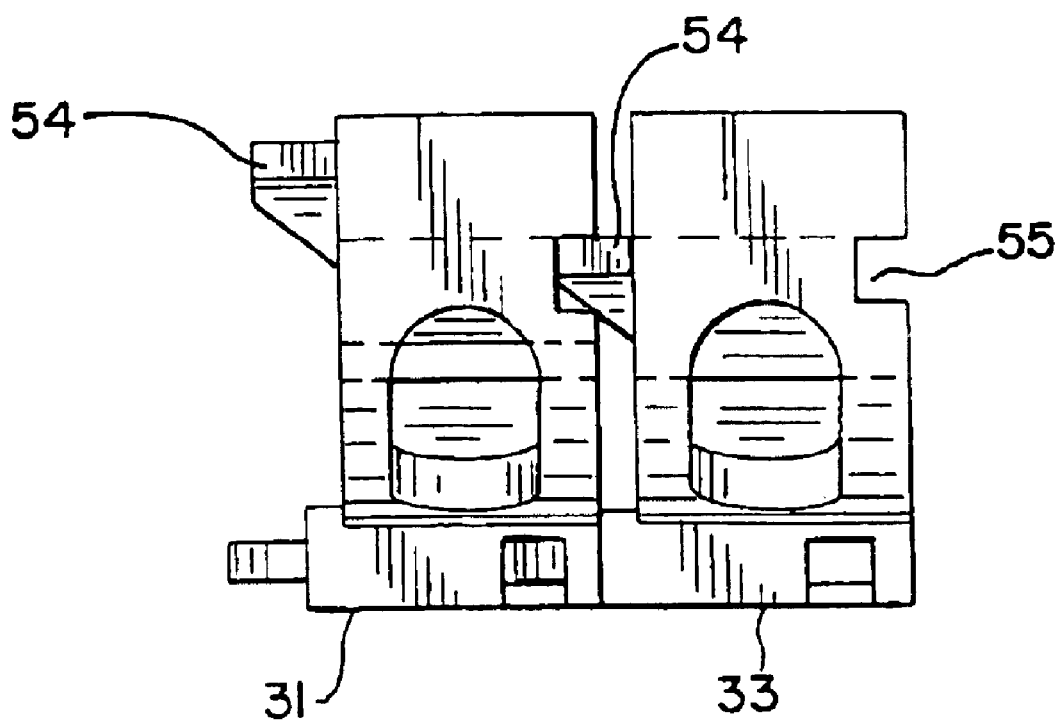

FLOW CONTROL DEVICE

The present invention is directed to a device for controlling the flow of liquid through two or more flexible tubes. The present invention finds particular application in the field of blood donation and in the tubing sets or fluid circuits used for such donations.

BACKGROUND

A disposable plastic tubing set or fluid circuit is typically used for collecting blood from a donor. The disposable tubing set includes a venipuncture needle for insertion into the arm of the donor. The needle is attached to one end of a flexible plastic tube which provides a flow path for the blood. The other end of the plastic tube is attached to one or more plastic bags or containers for collecting the withdrawn blood.

The blood tubing set may also include a sampling sub-unit. The sampling sub-unit allows for collection of a sample of blood, which sample can be used for testing of the blood. Preferably, the sample is obtained prior to the "main" collection of blood. Collecting the sample prior to the main collection reduces the risk that bacteria residing on the donor's skin where the needle is inserted (i.e., in particular, the small section of detached skin commonly referred to as the "skin plug") will not enter the collection container and contaminate the blood collected for transfusion. Thus, it is preferred that the blood sample, which may include the skin plug, be diverted from the main collection container.

An example of a blood tubing set with such a "pre-donation" sampling sub-unit is described in U.S. patent application Ser. No. 09/364,628 filed Jul. 29, 1999 and U.S. patent application Ser. No. 09/492,060 filed Jan. 27, 2000, which are incorporated by reference herein. The tubing sets described therein include a needle and a length of tubing, one end of which is attached to the needle and the other end of which is attached to one or more collection containers. The tubing set also includes an additional line which is branched from the main line at a Y-connection site in the tubing set. The branched line is attached to a sampling pouch for collecting a selected volume of blood from which samples may be obtained.

The tubing set described above also includes multiple and separate flow control devices for controlling the flow of biological fluid (e.g., blood) through the tubing set and to the sampling pouch and/or collection container. Flow control devices commonly used are the Roberts-type clamps, which are well known in the art. The Roberts-type clamps are placed on the tubing line leading to the blood collection container and on the tubing line leading to the sampling pouch. A Roberts-type clamp generally comprises a single strip of plastic where the ends of the strip are curved toward each other to engage each other in a snap-fit, spring relation. The body of the clamp includes a pair of apertures through which the tubing passes. The clamp further includes a pair of projections which compress the tubing when the body of the clamp is depressed, thereby restricting flow through the tube. Clamps of this type are generally described in U.S. Pat. Nos. 3,942,228 and 6,089,527, both of which are incorporated herein by reference.

By selectively opening and closing the different flow paths (by depressing or releasing the clamps), the technician can control the flow of blood from the donor, diverting the blood to the desired container or sampling pouch, as necessary. For example, in a pre-donation sampling, the flow path leading to the collection container may be initially compressed and closed, while the flow path leading to the sampling pouch remains open. Once a sufficient volume of blood has been collected in the sampling pouch, the flow path leading to the sampling pouch may be closed and the flow path leading to the collection container may then be opened. As noted above, a "pre-donation" sampling prevents the skin plug from entering the collection container and instead, diverts it to the sampling pouch, where blood that will not be transfused to a patient is collected.

Another example of a fluid circuit or tubing set with a sampling unit is described in International Application No. WO 00/24313. That publication describes a tubing set which also allows for diversion of a quantity of blood from a donor to a sampling sub-unit. The system includes a device that allows the technician to direct the blood or other biological fluid to either the blood collection container or to the sampling sub-unit. The device includes a housing that has an inlet and two or more outlet ports, with tubes connected to the inlet and outlet ports. By turning a knob on the flow control device, flow communication can be established between the inlet and one or the other of the outlet ports, as necessary. The flow control device described above overcomes the inconvenience of having to separately open and clamp off the different lines of the tubing set.

While the flow control devices described above have worked satisfactorily, further improvements in selectively controlling the flow of blood or other biological fluid through a tubing set are desired. For example, it would be desirable to provide a flow control device that is inexpensive and easy to manufacture, easily adaptable for use with two or more tubes, and easy to use by the technician.

SUMMARY OF THE INVENTION

In one aspect, the present invention is directed to a flow control device that includes a first clamp having a body with a first end and a second end. The ends of the first clamp are adapted for locking engagement with each other. The first clamp further includes at least two apertures in the body for receiving a flexible tube and a tubing contacting member for compressing a flexible tube. The flow control device also includes a second clamp in association with the first clamp. The second clamp, likewise, includes a body having first and second ends which are adapted for locking engagement with each other. The second clamp also includes at least two apertures for receiving a flexible tube and at least one tubing contacting member for compressing a tube. The second clamp further includes a releasing member for releasing the first clamp from the compressed position.

In another aspect, the present invention is directed to a flow control device having a body with a first and second end wherein the ends are adapted for locking engagement with each other. The flow control device includes at least two apertures in the body for receiving a flexible tube and at least one tubing contacting member for compressing a flexible tube. The flow control device also includes a connector for mating with a receiving member of another flow control device and a receiving member for mating with a connector of another flow control device.

In a further aspect, the present invention is directed to a flow control device that includes a body having a first end and a second end wherein the first end includes a notch and the second end includes a lip adapted for engagement with the notch. The second end further includes an extension that is laterally and axially spaced from the portion of the lip adapted for engagement with the notch.

In still another aspect, the present invention is directed to a flow control device that includes a first clamp and a second clamp adjacent to and in association with the first clamp. The first clamp includes a body having a first end and a second end, wherein the first end comprises a notch and the second end comprises a lip that is adapted for engagement with the notch. The first clamp includes at least two apertures in the body for receiving a flexible tube and at least one tubing contacting member for compressing a flexible tube. The second clamp, likewise, includes a body having a first end and a second end wherein the first end comprises a notch and the second end comprises a lip adapted for engagement with the notch. The lip of the second clamp further includes an extension that is adapted for contact with the first clamp end.

BRIEF DESCRIPTION OF THE DRAWINGS

FIG. 3 is a perspective view of a single clamp flow control device embodying the present invention;

FIG. 4 is a perspective view of a multiple clamp flow control device embodying the present invention;

FIG. 5 is a perspective view of the flow control device of FIG. 4 with the clamps detached;

FIG. 9 is a top plan view of a multiple clamp flow control device embodying the present invention with one clamp in an open position and the other clamp in the depressed and locked position;

FIG. 10 is a side view of the flow control device of FIG. 9;

FIG. 11 is a top plan view of a multiple clamp flow control device embodying the present invention with one of the clamps in a partially depressed position and the other clamp during release from the depressed and locked position;

FIG. 12 is a side view of the flow control device of FIG. 11;

FIG. 13 is a top plan view of a multiple clamp flow control device embodying the present invention with both clamps in the depressed and locked position; and FIG. 14 is a side view of the flow control device of FIG. 13; and FIG. 15 is an end view of a multiple clamp flow control device with one clamp in the depressed and locked position.

DETAILED DESCRIPTION OF THE DRAWINGS

Figure 1:
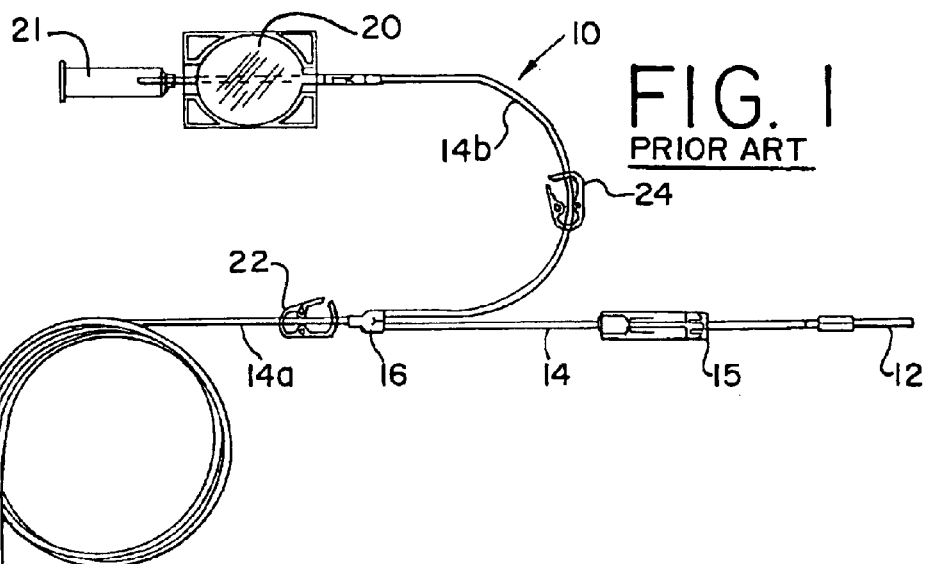
FIG. 1 is a perspective view of a prior art blood tubing set including a collection container and a sampling sub-unit.

Turning now to the drawings, FIG. 1 depicts a blood tubing set 10 of known type that is used in the collection of blood from a donor. Tubing set 10 includes a venipuncture needle 12 and a length of tubing 14. Tubing 14 branches at Y-connector 16 into tubing segment 14a and tubing segment 14b. Tubing segment 14a provides a flow path to a collection container 18 and tubing segment 14b provides a flow path to a sampling pouch 20. The sampling pouch may also include a holder 21 for receiving a blood sampling vial or tube. (Also shown is a needle protector 15 for storing the needle after use.)

In the blood tubing sets of the type shown in FIG. 1, tubing segments 14a and 14b are passed through flow control devices 22 and 24 which may be Roberts-type clamps. Such clamps are well known to those of skill in the art and have been previously described. During use of the tubing set of FIG. 1, the technician alternately opens and closes clamps 22 and 24 to direct the flow of blood into container 18 or sampling pouch 20.

Figure 2:
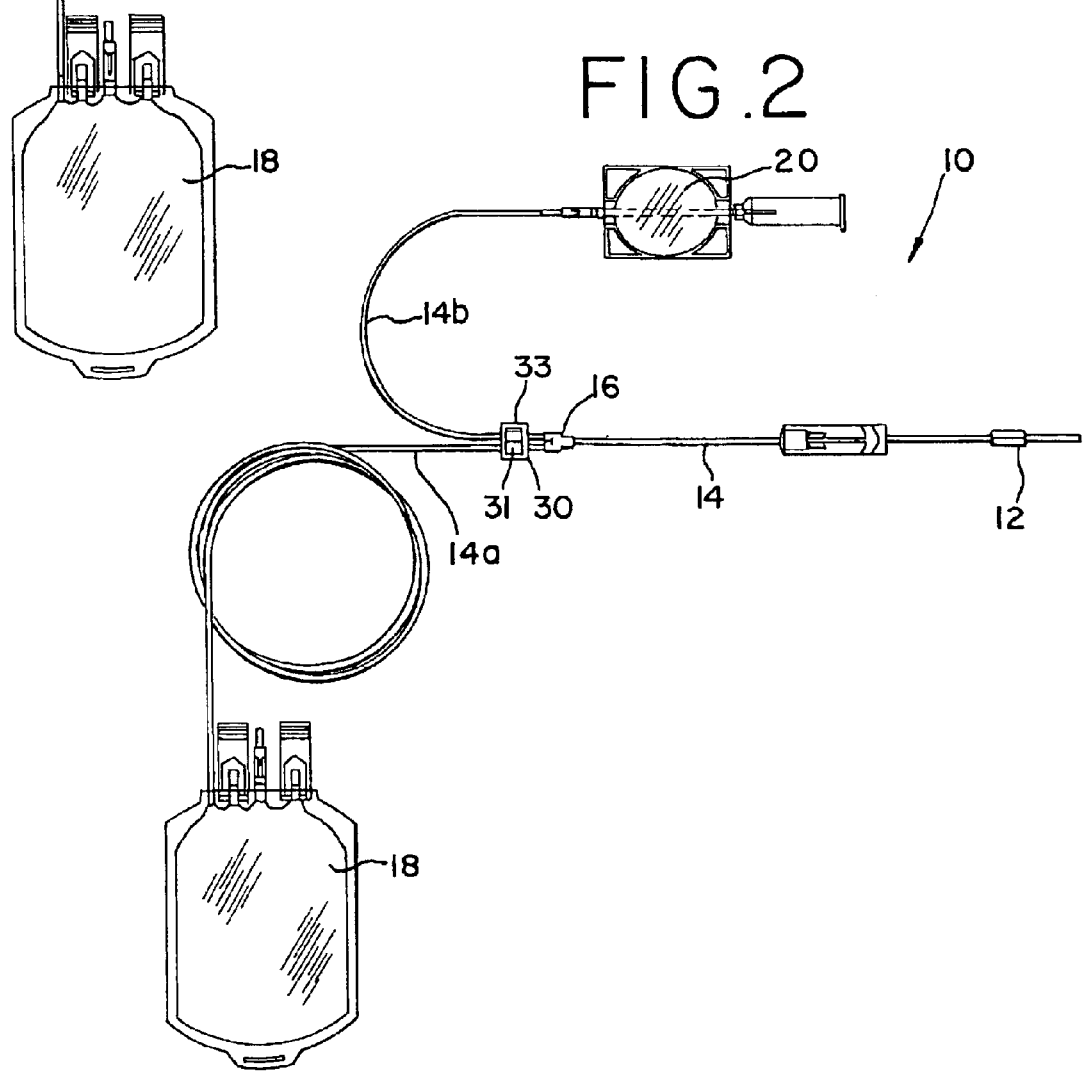
FIG. 2 is a perspective view of a blood tubing set for use with the flow control device of the present invention.

FIG. 2 shows a blood tubing set that includes a flow control device embodying the present invention. The tubing set 10 shown in FIG. 2, likewise, includes venipuncture needle 12, tubing 14 with tubing segments 14a and 14b providing flow paths to a collection container 18 and a sampling pouch 20, respectively. Flow control device embodying the present invention is generically shown as 30 in FIG. 2. More detailed views of the flow control device 30 of the present invention are shown in FIGS. 3 through 15.

As shown in FIG. 2, the flow control device 30 of the present invention is preferably placed on the tubing segments 14a and 14b just downstream of the Y-connector 16. In a preferred embodiment, the flow control device of the present invention includes two (or more) side-by-side, attached clamps 31 and 33 (FIG. 4). Each clamp 31 and 33 of flow control device 30 receives one of the tubing segments 14a or 14b. Of course, the flow control device 30 of the present invention may also be embodied in a single clamp (31) for use with a single tubing segment. Thus, the term "flow control device" is used to describe a device that includes one clamp or more than one clamp.

In accordance with the present invention, each clamp may be substantially identical to the adjacent clamp, and in a preferred embodiment of a multiple clamp flow control device, the clamps are structurally identical. Accordingly, the description that follows pertains to either clamp 31 or 33 (or any additional clamp) that may be part of multiple clamp flow control device 30.

Turning now to FIG. 3, clamp 31 (or 33) of flow control device 30 includes a curved, bent or otherwise non-linear body 32, made of semi-flexible, moldable plastic. Examples of suitable materials for molding the clamps of the flow control device include polypropylene, polyisoprene, or other plastic compositions that can be used in the manufacture of devices that are openable and closeable in a snap-fit manner.

As shown in FIG. 3, body 32 includes a first end 34 and a second end 36. As indicated above, body 32 may be curved or bent so that second end 36 is adjacent to but spaced from the first end 34. Clamp 31 (or 33) also includes apertures 38 and 40 for receiving the flexible tubes 14a or 14b. As further shown in FIGS. 3 and 4, clamp 31 (or 33) includes tube contacting members 42 and 44. In one embodiment, members 42 and 44 may be projections or teeth which pinch the flexible tubing 14 to restrict flow therethrough. Of course, it will be appreciated that other means for compressing the tubing or otherwise restricting flow through tubing 14 are also within the scope of the flow control device of the present invention. For example, tube contacting members 42 and 44 may be blunted or more rounded. Alternatively, flow control device 30 may include a single tube contacting member.

Figure 6:
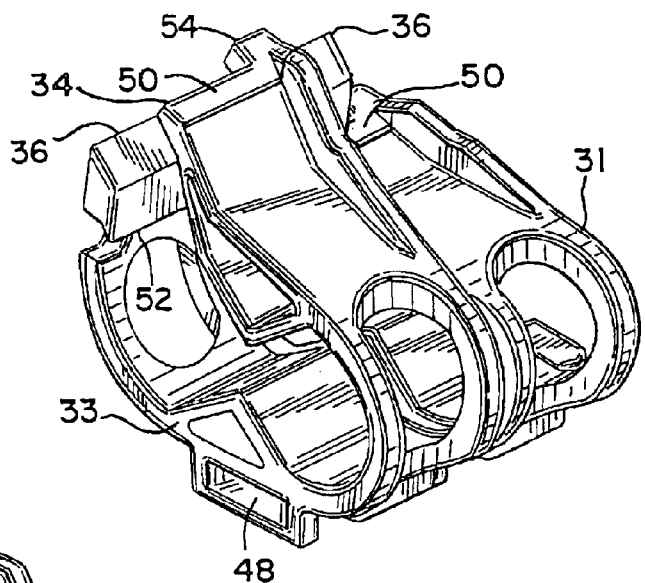
FIG. 6 is a perspective view of the flow control device of FIG. 4 with one of the clamps in the depressed and locked position and the other clamp in an open position.
Figure 7:
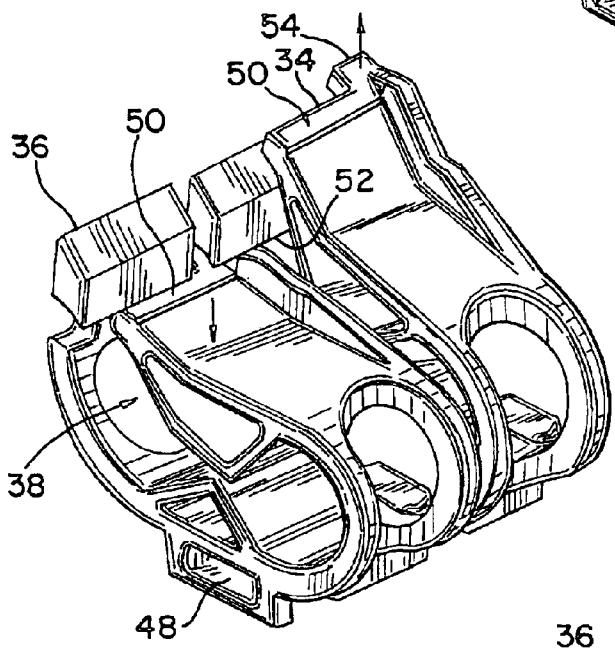
FIG. 7 is a perspective view of the flow control device of FIG. 4 with one of the clamps released from the depressed and locked position and the other clamp in the depressed and locked position.
Figure 8:
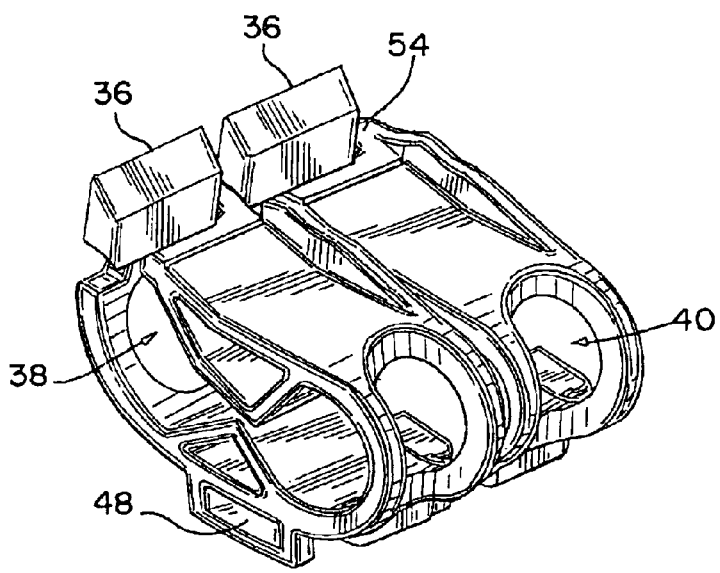
FIG. 8 is a perspective view of the flow control device of FIG. 4 with both clamps in the depressed and locked position.

As further shown in FIGS. 3 and 4, clamp 31 (or 33) includes a connector 46 and a receiving member 48 (shown, for example, in FIGS. 6–8). Connector 46 and receiving member 48 may be mated or otherwise cooperate with each other to allow attachment of one clamp 31 to another clamp 33.

First end 34 and second end 36 of the clamps are adapted for interlocking engagement with each other. This allows the technician to restrict flow through a tube without having to maintain manual pressure on the clamp. In one embodiment, shown in FIGS. 3 and 4, first end 34 includes a lip 50, while second end 36 includes a notch 52 for receiving lip 50. As best seen in FIGS. 7 and 9, when downward pressure is applied to the body 32 of the clamp 31 or 33, lip 50 pushes against and outwardly deflects second end 36. To further facilitate such outward deflection, end 36 may be chamfered. Continued downward movement of lip 50 results in the lip 50 being captured by notch 52 in an interlocking, snap-fit arrangement. This causes tube contacting members 42 and 44 to compress tubing 14, thereby restricting flow of liquid therethrough.

Returning briefly to FIG. 3, clamp 31 (33) of flow control device 30 includes an extension 54 that extends from lip 50 of the first end 34. In one embodiment, extension 54 extends outwardly, both laterally and axially (relative to axis line 60) from lip 50 (see, for example, FIGS. 9, 11 and 13). Extension 54 is also spaced from that portion of lip 50 which engages notch 52 of second end 36.

Clamp 31 (33) also may include a cut-out or slot 55 in body 32 near first end 34. FIG. 15 is a front view of a multiple clamp flow control device 30 with slots 55. As described in more detail below, when body 32 of clamp 33 is depressed (to restrict flow through a tube extending therethrough), extension 54 is captured within slot 55 of adjacent clamp 31, thereby locking clamp 33 in a restricted flow position.

As shown in FIGS. 9, 11 and 13, a portion of body 32 of clamp 31 (or 33) may be offset relative to the remainder of body 32. In particular, the portion 62 of body 32 between end 34 and aperture 38 may be offset. Thus, extension 54 is beyond the notch and substantially avoids contact with the notch of the same clamp. As shown in FIG. 9, the offset portion may be offset at a sharp angle from the remainder of the body 32 and axis 60, or may be otherwise offset by a more gradual curvature of the body portion.

Turning briefly to FIG. 4, two (or more) clamps can be attached to each other to provide a multiple clamp flow control device 30 of the present invention. As shown in FIGS. 4–7, connector 46 of clamp 33 is received by receiving member 48 of an adjacent clamp 31. In a preferred embodiment, the connector 46 may be a male member such as a prong, spike or winged connector which fits into a female-type slot such as receiving member 48 of an adjacent clamp in a snap-fit arrangement. Of course, it will be understood that other means of attaching or mating the two clamps to each other may also be used. For example, two adjacent clamps may be bonded to each other or alternatively connected. When connected to each other, the clamps of flow control device 30, allow for one-handed operation by the technician of the flow control device, described in more detail below.

For example, during a blood collection procedure (using a blood tubing set of the type shown in FIG. 2), clamp 31 of the flow control device 30 may initially be placed in a depressed and locked position, thereby compressing tubing segment 14a and restricting flow to collection container 18. Clamp 33, on the other hand, remains in the open position allowing blood to flow from the donor to a sampling pouch 20. FIGS. 9 and 10 show, in greater detail, the relative positions of clamps 31 and 33 during this initial blood sampling step. When a sufficient volume of blood has been collected in the sampling pouch, line 14b is then closed by depressing body 32 of the second clamp 33. As the body 32 of clamp 33 is depressed, lip 50 deflects second end 36 of clamp 33 outwardly until lip 50 is captured within notch 52.

In addition, during downward movement of the first end 34 of clamp 33, extension 54, which is laterally spaced from the portion of lip 50 that is to be captured within notch 52, deflects the second end 36 of adjacent first clamp 31 in an outward direction, as shown in FIGS. 11 and 12. As extension 54 outwardly deflects the end 36 of the adjacent clamp 31, it releases lip 50 from notch 52 (of clamp 31), resulting in the release of first clamp 31 from the depressed and locked position, also shown in FIG. 11. As second clamp 33 is depressed further, extension 54 of the second clamp 33 is captured within slot 55 of the adjacent first clamp 31, thereby holding and locking second clamp 33 in the restricted flow position. Clamp 33, with extension 54 captured within slot 55 of adjacent clamp 31 is shown in FIGS. 13 and 15.

Once a sufficient amount of blood has been collected in container 18, first clamp 31 may be depressed, until lip 50 is captured by notch 52 on the first clamp 31. Accordingly, both clamps are held in a restricted flow position, as generally shown in FIGS. 13–14.

As set forth above, extension 54 of clamp 33 avoids contact with second end 36 of clamp 33. Instead, and due in part to the offset (62), extension 54 contacts second end 36 of clamp 31 and is captured within slot 55 of clamp 31. Thus, it will be appreciated that operation of clamp 33 simultaneously allows for opening of tubing segment 14a and closure of the tubing 14b in one action. The relative positions (and proximity) of clamps 31 and 33 also allows the technician to open and/or close ("toggle" between) the clamps (and selectively control the flow of fluid) quickly and with relative ease.

Thus, an easy to use flow control device is provided. This flow control device can be made of inexpensive molded plastic with minimal moving parts. The flow control device is external to the tubing and does not require that the tubing segments leading to and from the containers and the venipuncture needle be bonded to the flow control device. In addition, because flow control device 30 is adapted for external placement on the tubing, separate sterilization of the device is not required. Moreover, further economies are realized in that the flow control device includes two or more clamps that are identical in shape and construction. Thus, the same mold and molding equipment can be used to make all clamps of the flow control device.

Multiple clamps relatively positioned can be employed together in a way that eliminates separate manual opening and closing of individual clamps. Also, two, three, four and possibly more clamps can be relatively positioned (e.g., connected in parallel) to provide the technician with easy, one-handed flow control of several flow paths. The different clamps can be color-coded or otherwise identified to ensure proper flow control.

The above description has been offered for illustrative purposes only and is not intended to limit the scope of this application, which is defined in the claims below.

That which is claimed:

1. A flow control device comprising:
a first clamp comprising a body having a first end and a second end, said ends adapted for locking engagement with each other, a pair of apertures in said body for receiving a flexible tube, and at least one tubing contacting member for compressing said flexible tube; and
a second clamp, in association with said first clamp, said second clamp comprising a body having a first end and a second end, said ends adapted for locking engagement with each other, a pair of apertures in said body for receiving a flexible tube, at least one tubing contacting member for compressing said flexible tube, and a releasing member for releasing said first clamp from a compressed position,
wherein said first and second clamps are relatively positioned to allow said releasing member to contact said first clamp.

2. Flow control device of claim 1 wherein said first and second clamps comprise an integral unit.

3. Flow control device of claim 1 wherein said first and second clamps are separate units attached to each other.

4. Flow control device of claim 3 wherein said first clamp comprises a connector and said second clamp comprises a slot for receiving said connector.

5. Flow control device of claim 1 wherein said first and second clamps are identical.

6. Flow control device of claim 1 wherein said releasing member comprises an extension on one of said second clamp ends.

7. Flow control device of claim 1 wherein compression of said second clamp closure member releases said first clamp from said compressed position.

8. Flow control device of claim 1 wherein said first and second clamps are molded from a polymeric material selected from the group consisting of polypropylene and polyisoprene.

9. Flow control device of claim 1 comprising a pair of oppositely facing pinching members for compressing a flexible tube.

10. A flow control device comprising:
a body having a first end and second end, said ends adapted for locking engagement with each other;
at least two apertures in said body for receiving a flexible tube therethrough;
at least one tubing contacting member for compressing said flexible tube,
a connector for mating with a receiving member of an adjacent flow control device; and
a receiving member for mating with a connector of an adjacent flow control device.

11. Flow control device of claim 10 wherein said first end comprises a notch and said second end comprises a lip adapted for engagement with said notch.

12. Flow control device of claim 11 wherein said lip comprises an extension laterally spaced from the portion of said lip that engages said notch.

13. Flow control device of claim 10 comprising a pair of oppositely facing pinching members for compressing said flexible tube.

14. Flow control device of claim 10 wherein said device is made of a material selected from the group consisting of polyisoprene and polypropylene.

15. A flow control device comprising:
a body having a first end and a second end wherein said first end comprises a notch and said second end comprises a lip adapted for engagement with said notch, wherein at least a portion of said body including said second end is offset from the remainder of said body, said second end portion further comprising an extension laterally spaced from and axially extending beyond the portion of said lip adapted for engagement with said notch.

16. Flow control device of claim 15 comprising means for attaching said device to another flow control device.

17. Flow control device of claim 15 comprising means for attaching said device to another identical flow control device.

18. Flow control device of claim 15 comprising a pair of oppositely facing pinching members for compressing a flexible tube.

19. Flow control device of claim 15 wherein said device is made of a material selected from the group consisting of polyisoprene and polypropylene.

20. A flow control device comprising:
(a) a first clamp comprising:
a body having a first end and a second end, wherein said body comprises a notch and slot in proximity to but spaced from said first end and said second end comprises a lip adapted for engagement with said notch, at least two apertures in said body for receiving a flexible tube, and at least one tubing contacting member for compressing a flexible tube; and
(b) a second clamp, adjacent to and in association with said first clamp, said second clamp comprising:
a body having a first end and a second end, wherein said first end comprises a notch and said second end comprises a lip adapted for engagement with said notch, said lip further comprising an extension adapted for locking engagement with said slot of said first clamp, at least two apertures for receiving a flexible tube, at least one tubing contacting member for compressing a flexible tube; and
wherein said extension is adapted for contact with said first end of said first clamp to release said first clamp lip from said first clamp notch.

21. Flow control device of claim 20 wherein said first clamp comprises a slot for receiving said extension.

22. Flow control device of claim 20 further comprising at least one additional clamp adjacent to and in association with either said first or second clamps.

23. A flow control device comprising:
a first clamp comprising a body having a first end and a second end, said ends adapted for locking engagement with each other, a pair of apertures in said body for receiving a flexible tube, and at least one tubing contacting member for compressing said flexible tube;
a second clamp, in association with said first clamp, said second clamp comprising a body having a first end and a second end, said ends adapted for locking engagement with each other, a pair of apertures in said body for receiving a flexible tube, at least one tubing contacting member for compressing said flexible tube;
wherein said first and second clamps are relatively positioned such that engaging said first and second ends of one of said first and second clamps causes disengaging of said first and second ends of said other of said first and second clamps.

24. A flow control system comprising:
a first clamp comprising a body having a first end and a second end, said ends adapted for locking engagement with each other, a pair of apertures in said body, a flexible tube defining a flow path and extending through said apertures, and at least one tubing contacting member for compressing said flexible tube to close said flow path;
a second clamp, in association with said first clamp, said second clamp comprising a body having a first end and a second end, said ends adapted for locking engagement with each other, a pair of apertures in said body, a flexible tube defining a flow path and extending through said apertures of said second clamp, at least one tubing contacting member for compressing said flexible tube to close said flow path;
wherein said first and second clamps are relatively positioned such that closing one flow path of said first and second clamps causes opening of said other flow path of said first and second clamps.

* * * * *